United States Patent [19]

Gaitanopoulos et al.

[11] Patent Number: 4,861,771

[45] Date of Patent: Aug. 29, 1989

[54] CARBAMATES OF 6-CHLORO-7,8-DIHYDROXY-1-(4'-HYDROXYPHENYL)-2,3,4,5-TETRAHYDRO-1H-3-BENZAZEPINE AS PRODRUGS

[75] Inventors: Dimitri Gaitanopoulos, Eagleville, Pa.; Bruce Mico, Bridgewater, N.J.; Joseph Weinstock, Phoenixville, Pa.

[73] Assignee: SmithKline Beckman Corporation, Philadelphia, Pa.

[21] Appl. No.: 303,519

[22] Filed: Jan. 27, 1989

[51] Int. Cl.$^4$ .................... C07D 223/16; A61K 31/55
[52] U.S. Cl. ..................................... 514/213; 540/595
[58] Field of Search ....................... 540/595; 514/213

[56] References Cited

U.S. PATENT DOCUMENTS 4,197,297  4/1980  Weinstock ........................ 424/244

FOREIGN PATENT DOCUMENTS 0005299  11/1979  European Pat. Off. ............ 514/213

Primary Examiner—David B. Springer
Attorney, Agent, or Firm—Joseph A. Marlino; Stuart R. Suter; Alan D. Lourie

[57] ABSTRACT

Prodrug carbamate derivatives of fenoldopam which provide fenoldopam plasma levels of similar magnitude and over a much longer period of time than the parent compound. An absence of a high initial peak effect associated with the parent compound is noted. A lead compound of the series is 6-chloro-7,8-diethylcarbamoyl-1-(4'-ethylcarbamoylphenyl)-2,3,4,5-tetrahydro-1H-3-benzazepine. The R-enantiomers are the most biologically active and preferred compounds.

16 Claims, No Drawings

CARBAMATES OF 6-CHLORO-7,8-DIHYDROXY-1-(4'-HYDROXY-PHENYL)-2,3,4,5-TETRAHYDRO-1H-3-BENZAZE-PINE AS PRODRUGS

BACKGROUND OF THE INVENTION

This invention relates to 6 Chloro-7,8-dihydroxy-1-(4'-hydroxyphenyl) 2,3,4,5-tetrahydro-1 H-3-benzazepine carbamates as prodrugs and their use as antihypertensive agents.

Prodrugs are biologically reversible derivatives which revert back to the parent molecule by virtue of enzymatic and/or chemical lability. They utilize a chemical molecule of proven biological activity (parent molecule) and deliver it to the site of action while overcoming some inherent drawback to the use of the parent compound. Prodrugs are chemical modifications which result in improved pharmaceutical, physiochemical and pharmacalogical properties and yet retain their desired biological activity.

Certain 6 halo-7,8-dihydroxy-1-(p-hydroxyphenyl)-2,3, 4,5-tetrahydro-1H-3-benzazepines are described in U.S. Pat. No. 4,197,297 to have antihypertensive activity by means of their peripheral dopaminergic effect. The leading species described there is the 6-chloro-congener known as fenoldopam. A limiting factor for the clinical use of fenoldopam orally is its low bioavailability due to its high first pass metabolism. This results in an initial high peak plasma level. The half life associated with fenoldopam is reportedly short and frequent dosing is necessary to sustain effective plasma concentrations with an oral dosing regimen.

It has been unexpectedly discovered that certain the carbomate derivatives of fenoldopam were administered to dogs they provided therapeutic plasma levels of the compound over a much longer period of time than the parent ccmpound itself. An absence of a high initial peak effect associated with the parent compound was also noted. The fenoldopam carbanates of this invention have the following structural formula:

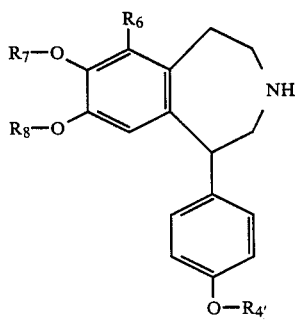

in which $R_6$ is halo and $R_7$, $R_8$ and $R_4$, are each independently hydrogen or CONHR where in R is a lower alkyl having from one to four carbon atoms. Preferably $R_7$, and $R_8$ are $COHC_2H_5$ and $R_4$, is hydrogen. Another advantageous compound of this invention is the trisethyl carbamate having the basic structural formula:

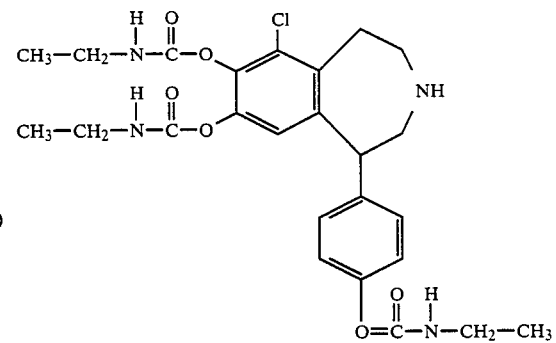

The pharmaceutically acceptable acid addition salts having the utility of the free bases of Formula I are part of this invention. They are prepared by methods well known to the art and are formed with both inorganic or organic acids, for example: maleic, fumaric, benzoic, ascorbic, pamoic, succinic, bismethylenesalicylic, methanesulfonic, ethanedi-sulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, methanesulfonic, cyclohexysulfamic, phosphoric and nitric acids. The hydrohalic and especially methanesulfonic acid salts are of particular utility. Similarly the quarternary salts include those prepared from organic halides such as methyl iodide, ethyl iodide, benzyl chloride and the like.

It will be obvious to one skilled in the art that the compounds of Formula 1 may be present as diastereoisomers which may be prepared as the individual R or S optical isomers. Resolution of the optical isomers of a convenient methoxy intermediate may be accomplished by fractional crystallization of their salts with optically active acids from appropriate solvents. Specific methods of resolution and preparation of the R-enantiomer of fenoldopam are disclosed in Acta Pharmaceutica Suecica Suppl.2, 1983, pages 132–150. Unless otherwise specified herein or in the claims, it is intended to include all isomers, whether separated or mixtures thereof. Where isomers are separated, the desired pharmacological activity will usually predominate in one of the isomers. Preferably, the R enantiomer is used for the purposes of this invention.

The methods of using the new compounds of this invention for medical purposes manifest themselves in a number of ways. Broadly speaking a peripheral dopaminergic effect is induced in patients in need thereof. The compounds, for example, cause vasodilation of dopaminergically innervated blood vessels. The result is to induce an increased renal blood flow. The end result will be an antihypertensive effect on patients having elevated blood pressures or to maintain stabilized blood pressures in patients prone to elevated pressures. This assertion does not rule out that the end result may be partially due to another mechanism of action. Other clinical uses for fenoldopam are in the treatment of congestive heart failure and renal failure, and the new compounds will provide more prolonged therapy.

The renal blood flow of the compounds of Formula 1 was readily measured in female mongrel dogs which underwent chronic implantation of a renal flow probe and arterial Vascular-Acess-Port. Briefly, the dogs were anesthetizied and using standard aseptic techniques, a Transonic flow probe was placed around the left renal artery and the connector tunneled subcutaneously to the back of the dog. The Vascular-Access-Port was placed in the left femoral artery and the access portion tacked to the underlying muscle in the area of the paralumbar-fossa. The patency of the Vascular Access Port was maintained by weekly flushing of the catheter and locking with a 50% glucose 500 U/ml heparinized solution. Dogs were trained to lie quietly restrained on a board and the connector portion of the flow probe was exteriorized under local anesthesia and connected to a Transonic flowmeter. Renal blood flow was recorded continuously on a Gilson chart recorder. Mean arterial pressure was monitored directly from the Vascular-Access-Port using a 23 gauge butterfly. Mean arterial blood pressure and renal blood flow were recorded before and for 6 hr. after the oral or i.v. administration of the R-enantiomers of the parent compound (fenoldopam) and the prodrug of fenoldopam. At the end of the experiment, the flow probe connector was returned to its subcutaneous position and the skin incision closed with chromic gut and skin staples. The VAP was again flushed and a fresh heparin glucose lock established. Standard sterile procedures followed during the removal and replacement of the flow probe connector.

During the experiment post drug blood samples were withdrawn periodically in order to determine the plasma levels of the parent drug, i.e., fenoldopam plasma levels.

The parent compound R-6-chloro-7,8-dihydroxy-1-(4'-hydroxyphenyl)-2,3,4,5-tetrahydro-1H-3-benzazepine tested orally for renal blood flow in 4 dogs as described above resulted in a significant increase (80%) in renal blood flow. The effect was transient and renal blood flow had returned to control values within 60 minutes. The plasma fenoldopam level in these dogs peaked in 5 minutes and showed a similar transient response as was observed with the renal blood flow.

In contrast, oral administration of the R-enantiomer of Formula 11, resulted in a sustained (4–6 hours) increase in both renal blood flow and plasma fenoldopam.

The sustained increase in renal blood flow and plasma fenoldopam levels were not due to slow oral absorption since intravenous administration of this prodrug also gave similar results.

The half life for plasma fenoldopam after oral administration of fenoldopam and the R-enantioner of Formula II were 12 minutes and 4.6 hours respectively.

The pharmaceutical compositions of this invention having peripheral dopaminergic activity are prepared in conventional dosage unit forms by incorporating a compound of Formula I, an isomer or a pharmaceutically acceptable acid addition salt or derivative thereof, with a nontoxic pharmaceutical carrier according to accepted procedures in a nontoxic amount sufficient to produce the desired pharmacodynamic activity in a subject, animal or human. Preferably the compositions will contain the active ingredient in an active but nontoxic amount selected from about 10 mg to about 1.0 g, preferably about 50–500 mg of the active ingredient per dosage unit. This quanity depends on the relative potency of the basic compound, the specific biological activity desired, the route of administration and the conditions of the patient. The preferred compounds of this invention especially as the hydrochloride salts have been found to have good absorbability from the gastrointestinal tract so oral dosage forms are of prime importance here preferably selected from the dosage unit ranges given above. Intravenous or subcutaneous doses would be lower.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are syrup, peanut oil, olive oil, water and the like. Similarly the carrier or diluent may include any time delay material well known to the art, such as glyceryl monostearate or glyceryl distearate alone or with a wax. Such sustained release products as well as derivatives which may be gradually metabolized to the active parent can be employed to prolong the unique biological activity of the compounds of this invention.

A wide variety of pharmaceutical forms can be employed. Thus, if a solid carrier for oral administration is used the preparation can be tableted, placed in a hard gelatin capsule in powder, regular or sustained release pellet form, or in the form of a troche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing dopaminergic activity in accordance with this invention comprises administering internally to a subject in need of such activity a compound of formula I or a pharmaceutically acceptable acid addition salt thereof, usually combined with a pharmaceutical carrier, in a nontoxic amount sufficient to produce said activity as described above. The route of administration may be any route which effectively transports the active compound to the dopamine receptors which are to be stimulated such as orally or parenterally, the oral route being preferred. Advantageously, equal doses within the ranges given above will be administered several times, such as from two to five times, a day with the daily dosage regimen being selected from about 10 mg. to about 1.0 g. preferably 50 mg. to 2.0 g. for oral dosage units. When the method described above is carried out antihypertensive activity is produced. For an average size human for the preferred species (II) a preferred oral dose to show antihypertensive activity would be selected from the range of from about 25 to 500 mg. for each dosage unit adapted for oral administration to be administered from 1–5 times daily.

The following examples are designed solely to illustrate the preparation and use of the compounds of this invention. The temperatures are Centigrade. Other variations of these examples will be obvious to those skilled in the art.

EXAMPLE 1

27.0 g of the methanesulfonate salt of 6-chloro-7,8-dihydroxy-1-(4-hydroxyphenyl) 2,3,4,5-tetrahdyro-1H-3-benzazepine (fenoldopam) was dissolved in 150 ml. of DMF. Triethylamine (13.6 g) was added and the reaction was stirred for thirty minutes at ambient temperature. Di-t-butyl-dicarbonate 14.6 g) was added. The reaction was stirred for 2.5 hours at ambient temperature and then poured into water. The product was extracted with ethyl acetate and the organic extracts were washed with water, dried over anhydrous magnesium sulfate and concentrated. The oil was dissolved in 150 ml. of dichloromethane and the solution was allowed to stand undisturbed for 20 hours at ambient temperature.

The solid which formed was filtered and washed with cold dichloromethane to yield 3-t-butyloxycabonyl-6-chloro-7,8-dihydroxy-1-(4'-hydroxyphenyl)-2,3,4,5-tetrahydro-1 H-3-benzazepine, M.P. 201°–202° C.

The above benzazepine (15.0 g) was suspended in acetonitrile. 15.0 g of ethyl isocyanate was slowly added followed by the addition of 0.5 ml of triethylamine. The reaction was refluxed for one hour on a steam bath and concentrated. The resulting foam was triturated with petroleum ether to produce 3-t-butyloxycarbonyl-6-chloro-7,8-diethylcarbamoyl-1-(4'-ethylcarbamoylphenyl) 2,3,4,5-tetrahydro-1 H-3-benzazepine M.P. 89°–95° C.

A solution of 23.2 of the above butyloxycarbamoyl compound in 25 ml of methanol was cooled to 10° C. and treated with a stream of HCL gas for two minutes. The reaction mixture was stirred at ambient temperature for 6 hours and concentrated under reduced pressure. The resulting residue was twice dissolved in 200 ml of 1:1 methanol and methyleme chloride and the solvent removed under reduced pressure. The residue was dissolveiv in 200 ml of methanol and treated with 4 g of charcoal. The filtered methanol solution was concentrated under reduced pressure and the resulting residue crystallized from methanol-ethyl acetate to yield 6-chloro-7,8-diethylcarbamoyl-1-(4'-ethylcarbamoylphenyl) 2,3,4,5-tetrahydro-1-H-3-benzazepine hydrochloride, MP 208°–210° C.

EXAMPLE 2

Following the procedure of Example 1 and substituting the methane sulfonate salt of (R) 7,8-dihydroxy-6-fluoro-1-(4'-hydroxyphenyl)-2,3,4,5-tetrahydro-1H-3-benzazepine as the starting material gave (R)-3-t-butyloxycarbonyl-7,8-dihydroxy-6-fluoro-1-(4'-hydroxyphenyl)-2,3,4,5-tetrahydro-1-H-3-benzazepine as a foam, (R)-3-t-butyloxcarbonyl)-7,8-diethylcarbamoy-1-(4'-ethylcarbamoylphenyl)-6-fluoro-2,3,4,5tetrahydro-1H-3-benzazepine, M.P. 100°–105° C., and (R)-7,8-diethylcarbamoyl-1-(4'-ethylcarbomoylphenyl))-6-fluoro-2,3,4,5-tetrahydro-1H-3-benzazepine hydrochloride, M.P. 195°–200° C., respectively.

EXAMPLE 3

Following the procedure of Example 1 and substituting (R)-6-chloro-7,8-dihydroxy-I-(4'-hydroxyphenyl) 2,3,4,5-tetrahydro-1H-3-benzazepine hydrochloride as the starting material gave (R)-6-chloro-7,8-diethylcarbamoyl-(4'-ethylcarbamoylphenyl)-2,3,4,5-tetrahydro-1H-3-benzazepine hydrochloride, M.P. 180°–195° C.

EXAMPLE 4

10.0 g of 3-t-butyloxycarbonyl-6-chloro-7, 8-dihydroxy-1-(4'-hydroxyphenyl) 2,3,4,5-tetrahydro-1H-3-benzazepine was dissolved in 100 ml of DMF. To this was added 1.25 g of a 50% sodium hydride mineral oil dispersion under an argon atmosphere. The reaction was stirred at ambient temperature for 15 minutes and 3.59 g of 4-methozybenyl chloride was added. The reaction was stirred for 16 hours at ambient temperature then poured into a large volume of water. The mixture was then extracted with ethyl acetate. The extracts were washed with water dried over magnesium sulfate and concentrated to yield an oil. The crude product was dissolved in 100 ml. of acetonitrile and the solution washed with several portions of petroleum ether. The acetonitrile solution was concentrated and seeded with crystals of the product. The solution was allowed to stand in a freezer overnight with a resultant of white solid. Additional solid was obtained after concentration of the mother liquor. The solid (5.57 g) was heated for 10 minutes in 100 ml of dichloromethane on a steam bath. The suspension was filtered and the solid washed with warm dichloromethane to yield 3-t-butyloxycarbonyl-6-chloro-8-hydroxy-7-(4-methoxybenzyloxy)-1-(4 -hydroxyphenyl)-2,3,4,5 tetrahydro-1-H-3-benzazepine, M.P. 190°–192° C.

The above benzazepine (3.12 g) was dissolved in 50 ml of dimethylformamide. Benzyl biomide was added followed by the addition of 0.65 g of 50% sodium hydride-mineral oil dispersion under an argon atmosphere. The reaction was stirred at ambient temperature and poured into a large volume of water. The mixture was extracted with ethyl acetate. The organic extracts were washed with water, dried over magnesium sulfate and concentrated. The crude product was purified by flash column chromatography with 4:1 hexane-ethyl acetate as the eluant to yield 3-t-butyloxycarbonyl-6-chloro-8-benzyloxy-7-(4'-benzyl-oxyphenyl) 2,3,4,5 tetrahydro-1H-3-benzazepine.

The above benzyloxy benzazepine (3.67 g), was dissolved in ethyl acetate (70 ml). Ethereal hydrogen chloride was added and the reaction was stirred at ambient temperature until the solution became cloudy. The solution was then allowed to stand at ambient temperature until crystallization was complete. The mixture filtered and the solid washed with ethyl acetate to yield 6-chloro-8-benzyloxy-7-hydroxy-1-(4'-benzyloxyphenyl)-2,3,4,5-tetrahydro-1H-3-benzazepine hydrochloride, M.P. 237°–240° C.

The above benzazepine hydrochloride (2.0 g) was dissolved in 10 ml of dimethylformamide. Triethylamine (1.1 ml)was added and the reaction stirred for 20 minutes at ambient temperature. Di-t-butyl-carbonate (0.83 g) was added. The reaction was stirred for 2 hours at ambient temperature then diluted with water. The product was extracted with ethyl acetate and the extracts were washed with water, dried over magnesium sulfate and concentrated. The 7-hydroxy intermediate (2.49 g) was dissolved in 50 ml of acetonitrile and 1.08 g of ethyl isocyanate and 0.1 nl of triethylamine were added. The reaction was heated for 2 hours on a steam bath and concentrated. The residue (2.94 g) was chromatographed with 2:1 hexane-ethyl acetate as the eluant to yield 3-t-butyloxycarbonyl-8-benzyloxy-6-chloro-7-ethylcarbamoyl-1-(4'-benzyloxyphenyl) 2,3,4,5-tetrahydro-1H-benzazepine.

The above 7-ethylcarbamoyl derivative 2.39 g (3.5 mml) was dissolved in 100 ml. of 1:2 methanol-ethyl acetate 230 mg. of 10% palladium on carbon was added and the mixture was hydrogenated at 50 PSI for 6 hours. The reaction was filtered and concentrated to yield the debenzylated 3-t-butyloxycarbonyl-6-chloro-7-ethylcarbamoyl-8-hydroxy-1-(4'-hydroxyphenyl)2,3,4,5 tetrahydro-1H-3-benzazepine. This compound (1.66 g) was dissolved in 100 ml of ethyl acetate. 15.0 ml of ethereal hydrogen chloride was added and the reaction stirred at ambient temperature until the solution became cloudy. The solution was allowed to stand for 16 hours until precipitation was complete. The mixture was filtered and the solid washed with ethyl acetate. The precipitate (1.33 g) was recrystallized from methanol-ethyl acetate to yield 6-chloro-7-ethylcarbamoyl 8-hydroxy-1-(4'-hydroxyphenyl)-2,3,4,5-tatrehydro-1H-3-benzazepine, M.p. 235°–237° dec.

EXAMPLE 5

3-t-butyloxycarbomyl-6-chloro 7,8-dihydroxy-1-(4'-hydroxyphenyl)-2,3,4,5- tetrahydro-1H-3-benzazepine was dissolved in 200 ml of DMF. To this was added under an argon atmosphere 3.6 g(0.077 ml) of 4-methoxybenzyl chloride followed by 3.6 (0.077 ml) of 50% sodium hydride-mineral oil 1.1 g (0.023 mal) were added and the reaction was stirred five hours at ambient temperature. The reaction was poured into a large volume of water and the product was extracted with ethyl acetate. The extracts were washed with water, dried over magnesium sulfate and concentrated. The residue was dissolved in 300 ml. of acetonitrile and the solution was washed with several portions of petroleum ether. The acetonitrile solution was concentrated, and allowed to stand for 52 hours in a freezer. The solid was filtered and washed with cold acetonitrile to yield 3-t-bulyloxycarbonyl-6-chloro-7,8-di (4-methoxybenzyloxy)-1-(4'-hydroxyphenyl) 2,3,4,5-tetrahydro-1H-3-benzazepine.

The above benzazepine was dissolved in 100 ml of DMF. To this solution was added 4.49 g of benzyl bromide and 1.25 g of 50% sodium hydride-mineral oil dispersion. The reaction was stirred for 16 hours under argon at ambient temperature then poured into a large volume of water. The extracts were washed with water dried over magnesium sulfate and concentrated. The crude product was purified by fresh column chromatography with 4:1 hexane ethyl acetate to yield 3-t-butyloxycarbonyl-6-chloro-7,8-di-(4-methoxybenzyloxy)-l-(4'-benzyloxyphenyl) 2,3,4,5-tetrahydro-1H-3-benzazepine 13.48 g (0.018 mol) of this compound was dissolved in 1:1 methanol-ethyl acetate (200 ml). To this solution was added 100 ml of ethereal hydrogen chloride and the reaction was stirred for 16 hours at ambient temperature. The reaction was concentrated and the residue triturated with acetonitrile. The solid was filtered and washed with cold acetonitrile yielding 6-chloro-7,8-dihydroxy-1-(4'-benzyloxyphenyl)2,3,4,5-tetrahydro-1H-3-benzazepine.

The above benzazepine 7.05 g (0.016 ml) was dissolved in 75 ml of DMF. To this was added 3.35 g (0.033 ml) of triethylamine and the reaction was stirred for 30 minutes at ambient temperature. 3.73 of di-t-butyldicarbonate was added and the reactiion stirred 3 hours at ambient temperature then poured into water. The product was exrracte'd with ethyl acetate and the extracts washed with water dried over magnesium sulfate and concentrated. The crude product was purified by flash column chromatography with 1.99 methanol-dichloromethane to yield 3-t-butyloxycarbonyl-6-chloro-7,8-dihydroxy-1-(4'-benzyloxyphenyl)-2,3,4,5-tetrahydro-1H-3-benzazepine. 9.15 g of this compound was dissolved in 100 ml of DMF. Benzyl bromide 1.7 lg and 0.48 g of a 50% sodium hydride-mineral oil dispersion were-added. The reaction was stirred 2 hours at ambient temperature under argon. Additional (0.85 g) benzyl bromide and 50% sodium hydydride-mineral oil (0.24 g) were added ans stirring was continued for 16 hours at ambient temperature. The reaction was poured into water and the mixture extracted with ethyl acetate. The extracts were washed with water, dried over magnesium sulfate and concentrated. The crude product mixture was chromatographed using 5:1 hexane-ethyl acetate to yield 3-t-butyloxycarbonyl-7-benzyloxy-6-chloro-8-hydroxy-1-(4'-benzyloxyphenyl) 2,3,4,5-tetrahydro-3-benzazepine. The crude product was purified by fresh column chromatography with 4:1 hexane ethyl acetate to yield 3-t-butyloxycarbonyl-6-chloro-7,8-di-(4-methoxybenzyloxy) 1-(4'-benzyloxyphenyl) 3,4,5-tetrahydro-1H-3-benzazepine 13.48 g (0.018 mol) of this compound was dissolved in 1:1 methanol-ethyl acetate (200 ml). To this solution was added 100 ml of ethereal hydrogen chloride and the reaction was stirred for 16 hours at ambient temperature. The reaction was concentrated and the residue triturated with acetonitrile. The solid was filtered and washed with cold acetonitrile yielding 6-chloro-7,8-dihydroxy-1-(4'-benzyloxyphenyl)2,3,4,5-tetrahydro-1H-3-benzazepine.

The above benzazepine 7.05 g (0.016 ml) was dissolved in 75 ml of DMF. To this was added 3.35 g (0.033 ml) of triethylamine and the reaction was stirred for 30 minutes at ambient temperature. 3.73 of di-t-butyldicarbonate was added and the reaction stirred 3 hours at ambient temperature then poured into water. The product was extracted with ethyl acetate and the extracts washed with water dried over magnesium sulfate and concentrated. The crude product was purified by flash column chromatography with 1.99 methanol-dichloromethane to yield 3-t-butyloxycarbonyl-6-chloro-7,8-dihydroxy-1-(4'-benzyloxyphenyl)-2,3,4,5-tetrahydro-1H-3-benzazepine. 9.15 g of this compound was dissolved in 100 ml of DMF. Benzyl bromide 1.7 g and 0.48 g of a 50% sodium hydride-mineral oil dispersion were added. The reaction was stirred 2 hours at ambient temperature under argon. Additional (0.85 g) benzyl bromide and 50% sodium hydydride-mineral oil (0.24 g) were added ans stirring was continued for 16 hours at ambient temperature. The reaction was poured into water and the mixture extracted with ethyl acetate. The extracts were washed with water, dried over magnesium sulfate and concentrated. The crude product mixture was chromatographed using 5:1 hexane-ethyl acetate to yield 3-t-butyloxycarbonyl-7-benzyloxy-6-chloro-8-hydroxy-1-(4'-benzyloxyphenyl) 2,3,4,5-tetrahydro-3-benzazepine.

2.4 g of the above 7-benzyloxy benzezapine was dissolved in 50 ml of acetonitrile. Ethyl isocyanate 1.3 g and 0.1 ml of triethylamine were added. The reaction was refluxed for 3 hours on a steam bath and concentrated. The residue (4.03 g) was chromatographed with 4:1 hexane-ethyl acetate to yield 3-t-butyloxycarbonyl-7-benzyloxy-6-chloro-8-ethylcarbayl-1-(4'-benzyloxyphenyl) 2,3,4,5-tetrahydro-3-benzazepine.

The above 8-ethylcarbamoyl benzazepine (2.0 g) was dissolved in 100 ml of 1:2 methanol-ethyl acetate. 230 g of 10% palladium on carbon was added and the mixture hydrogenated at 50 PSI for 6 hours. The reaction was filtered and concentrated to yield 3-t-butyloxycarbonyl-6-chloro-8-ethylcarbamoyl-7-hydroxy-1-(4'-hydroxyphenyl)2,3,4,5-tetrahydro-1H-3-benzazepine and 1.49 g of this compound was dissolved in 100 ml of ethyl acetate. To this solution was added 15.0 ml of ethereal hydrogen chloride and the reaction stirred at ambient temperature until the solution became cloudy. The solution was allowed to stand for 16 hours until precipitation was complete. The mixture was filtered and the solid washed with ethyl acetate. The precipitate was recrystallized from methanol-ethyl acetate to yield 6-chloro 8-ethylcarbamoyl-7-hydroxy-1-(4'-hydroxyphenyl)-2,3,4,5-tetrahydro-1H-3-benzazepine hydrochloride.

EXAMPLE 6

6-chloro-7,8-dihydroxy-1-(4'-benzyloxyphenyl)-2,3,4,5-tetrahydro 1H-3-benzazepine 0.98 g was dissolved in 10 ml of DMF. Triethylamine (1.1 ml) was added and the reaction was stirred for 20 minutes at ambient temperature. Di-t-butyl dicarbonate (0.83 g) was then added. The reaction was stirred for two hours at ambient temperature and diluted with water. The product was extracted with ethyl acetate.

Chromatography of the crude product on silica gel using 40% ethyl acetate/60% hexane gave (R)-3-t-butyloxycarbonyl-6-chloro-7-ethylcarbamoyl-8-hydroxy-1-(4'-hydroxyphenyl)-2,3,4,5-tetrahydro-1H-3-benzazepine. MP 170°–172° C.; TLC (E Merk silica gel 60, 1:1-EtOAC: Hexane; vv) Rf 0.31. 100 ml of trifluoroacetic acid was cooled to 5° C. under argon atmosphere and 12.2 g (0.0256 moles) of the above 7-ethyl carbamoyl compound was added with stirring. After stirring for 1 hour, the reaction mixture was concentrated under reduced pressure and chased with 100 ml of ethyl acetate. The resulting solid was dried under high vacum at 40° C. to give (R)-6-chloro 7-ethylcarbamoyl-8-hydroxy-1-(4'-hydroxyphenyl)-2,3,4,5-tetrahydro-1 H-3-benzazepine trifluoroacetate, M.P. 157°–159° C. The Rf and NMR of this material were similar to those of the corresponding racemic compound described in Example 3.

EXAMPLE 8

The chromatography of the crude carbamylation reaction mixture described in Example 6 gave as a second major component (R)-3-t-butyloxycarbonyl-6-chloro-7-hydroxy-8-ethylcarbamoyl-1-(4'-hydroxyphenyl)-2,3,4,5-tetrahydro-1H-3-benzazepine. M.P. 120°–125° C.; TLC (E Merck silica gel 60; 1:1-EtOAC:-hexane; vv) Rf 0.39.

Treatment of the above 8-ethylcarbamoyl derivative with trifluoroacetic acid as described in Example 6 yielded (R)-6-chloro-7-hydroxy-8-ethylcarbamyl-1-(4'-hydroxyphenyl)-2,3,4,5-tetrahydro-1H-3-benzazepine trifluoroacetate M.P. 165°–167° C. The Rf and NMR of this compound was similar to that of the corrresponding racemic compound described in Example 4.

EXAMPLE 9

The chromotography of the crude carbamylation reaction described in Example 6 gave as a third major component (R)-3-t-butyloxy-carbonyl-6-chloro-7,8-diethylcarbamoyl-1-(4'-hydroxyphenyl)-2,3,4,5-tetrahydro-1H-3-benzazepine. M.P. 128°–140° C., TLC (E Merck Silica gel 60, 1:1 EtOAC-hexane:vv) Rf 0.28.

A solution of 14.3 g(0.03 moles) of (R)-3-t-butyloxycarbonyl-6-chloro-7,8-diethylcarbamyl-1-(4'-hydroxyphenyl) 2,3,4,5-tetrahydro-1H-3-benzazepine, in 100 ml of ethyl acetate at 25° C. was treated with 50 ml of ethereal hydrogen chloride under argon atmosphere. After stirring for 72 hours, the reaction mixture was concentrated under reduced pressure and chased with 200 ml. of dry toluene. The resulting residue was triturated with 00 ml of ethyl acetate to give (R)-6-chloro-7,8-diethycarbamoyl-1-(4-hydroxyphenyl)-2,3,4,5-tetrahydro-1H 3-benzazepine hydrochloride, M.P. 185°–190° C. The Rf and the NMR of this compound was similar to that of the corresponding racemic compound of Example 5.

EXAMPLE 10

| INGREDIENTS | Mg./Capsules |
| --- | --- |
| (R)-6-chloro-7,8-diethylcarbamoyl-1 (4'-ethylcarbamoylphenyl)-2,3,4,5-tetrahydro-1H—3-benzazepine hydrochloride | 350 |
| Magnesium stearate | 2 |
| Lactose | 75 |

The above ingredients are thoroughly mixed and placed into hard gelatin capsules. One capsule is administered orally to subjects in need of treatmen- from 2 to 4 times daily.

EXAMPLE 11

| INGREDIENTS | Mg./Capsules |
| --- | --- |
| (R)-6-chloro-7,8-diethylcarbamoyl-1 (4'-hydroxyphenyl)-2,3,4,5-tetrahydro-1H—3-benzazepine hydrochloride | 150 |
| Corn Starch | |
| Polyvinylpyrrolidone | 30 |
| Magnesium Stearate | 5 |

The benzazepine and corn starch are granulated with the polyvinylpyrrolidone. The granules are dried mixed with the magnesium stearate and compressed into tablets. One tablet is taken from 2 to 5 times daily.

EXAMPLE 12

| INGREDIENTS | Mg./Capsules |
| --- | --- |
| 6-chloro-7-ethylcarbamoyl-8-hydroxy-1-(4'-hydroxyphenyl) 2,3,4,5-tetrahydro-1H—3-benzazepine trifluoroacetate | 500 mg |
| Magnesium Stearate | 3 mg |
| Lactose | 10 |

INGREDIENTS Mg./Capsules
The above ingredients are thoroughly mixed and placed into hard gelatin capsules. One capsule is administered 1 to 3 times daily for the treatment of hypertension.

What is claimed is:

1. A compound of the structural formula:

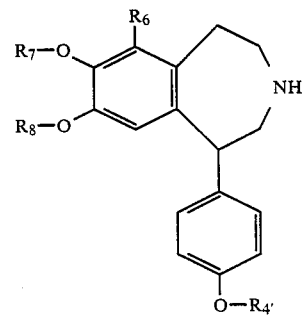

in which:
  $R_6$ is halo; and
  $R_7$, $R_8$ and $R_4$ are each independently hydrogen or —CONHR wherein R is lower alkyl having from one to four carbon atoms; or a nontoxic pharmaceutically acceptable acid addition salt thereof.

2. The compound of claim 1 in which $R_6$ is chloro.

3. The compound of claim 2 in which $R_4$, $R_7$ and $R_8$ are —CONHR.

4. The compound of claim 3 being 6-chloro-7,8-diethylcarbamoyl-1-(4'-ethylcarbamoylphenyl)-2,3,4,5-tetrahydro-1H-3-benzazepine or one of its pharmaceutically acceptable acid addition salts.

5. The compound of claim 4 being the R-enantiomer.

6. The compound of claim 4 being the hydrochloride salt.

7. The compound of claim 4 being the free base.

8. The compound of claim 2 in which $R_7$ and $R_8$ are CONHR and $R_4$ is hydrogen.

9. The compound of claim 8 being 6-chloro 7,8-diethylcarbamoyl-1-(4'-hydroxyphenyl)-2,3,4,5-tetrahydro-1H-3-benzazepine or one ot its nontoxic pharmaceutically acceptable acid addition salts.

10. The method of inducing peripheral dopaminergic activity in a subject in need thereof comprising administering orally a nontoxic dopaminergic quantity of a compound of claim 1.

11. The method of inducing antihypertensive activity in a subject in need thereof comprising administering orally or by injection a nontoxic antihypertensive quantity of a compound of claim 1.

12. The method of claim 10 in which the compound is (R)-6-chloro-7,8-diethylcarbamoyl-(4'-ethylcarbamoylphenyl)-2,3,4,5-tetrahydro-1H-3-benzazepine or one of its nontoxic pharmaceutically acceptable acid addition salts.

13. The method of claim 11 in which the route of administration is oral and the dosage unit is from about 50 to about 500 mg. of the compound.

14. A pharmaceutical composition having antihypertensive activity comprising a nontoxic antihypertensive quantity of a compound of claim 1.

15. The composition of claim 14 in which the compound is 6-chloro-7,8-diethylcarbamoyl-(4'-ethylcarbamoylphenyl)-2,3,4,5-tetrahydro-1H-3-benzazepine or one of its pharmaceutically acceptable acid addition salts.

16. The composition of claim 15 in which the compound is present as the R-enantiomer.

* * * * *